(12) United States Patent
Manzer

(10) Patent No.: US 6,617,464 B2
(45) Date of Patent: Sep. 9, 2003

(54) PRODUCTION OF 5-METHYLBUTYROLACTONE FROM LEVULINIC ACID

(75) Inventor: Leo E. Manzer, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/099,354

(22) Filed: Mar. 15, 2002

(65) Prior Publication Data

US 2003/0055270 A1 Mar. 20, 2003

Related U.S. Application Data

(60) Provisional application No. 60/276,581, filed on Mar. 16, 2001.

(51) Int. Cl.[7] ............................................. C07D 307/04
(52) U.S. Cl. ....................................................... 549/326
(58) Field of Search ........................................... 549/326

(56) References Cited

U.S. PATENT DOCUMENTS

| 2,786,852 | A | * | 3/1957 | Dunlop et al. ........... 260/343.6 |
| 4,420,622 | A | * | 12/1983 | Van de Moesdijk et al. ..... 549/326 |
| 5,883,266 | A | * | 3/1999 | Elliott et al. ................ 549/273 |

* cited by examiner

Primary Examiner—Joseph K. McKane
Assistant Examiner—Golam M. M. Shameem
(74) Attorney, Agent, or Firm—Inna Y. Belopolsky

(57) ABSTRACT

A process for producing 5-methylbutyrolactone from levulinic acid utilizing an optionally supported metal catalyst is described. The catalyst has both a hydrogenation and a ring-closing function.

15 Claims, No Drawings

PRODUCTION OF 5-METHYLBUTYROLACTONE FROM LEVULINIC ACID

This application claims benefit of 60/276,581.

FIELD OF INVENTION

This invention relates to a process for producing 5-methylbutyrolactone from levulinic acid utilizing an optionally supported metal catalyst.

BACKGROUND

Levulinic acid is a well-known product of hexose acid hydrolysis, and is inexpensively obtained from cellulose feedstocks. Consequently, it is an attractive starting material in producing many useful 5-carbon compounds such as methyltetrahydrofuran and derivatives. 5-methylbutyrolactone, also known as 5-valerolactone or γ-valerolactone, can be produced from levulinic acid as shown below.

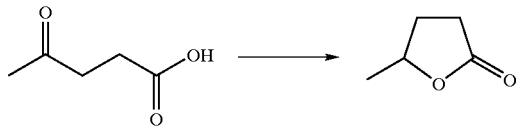

U.S. Pat. No. 5,883,266 discloses the use of a bifunctional catalyst having a first function of hydrogenating and a second function of ring opening to prepare a variety of products from levulinic acid including 5-valerolactone. U.S. Pat. No. 2,786,852 disclosed production of 5-valerolactone from levulinic acid using a reduced copper oxide catalyst. U.S. Pat. No. 4,420,622 discloses preparation of 5-alkyl-butyrolactones from levulinic esters using metal catalysts.

SUMMARY OF THE INVENTION

The present invention is a process of preparing 5-methylbutyrolactone comprising heating levulinic acid in the presence of hydrogen with a catalytic amount of a catalyst having a hydrogenation and a ring-closing function, wherein the catalyst is a metal. The metal catalyst is optionally supported on a catalyst support. Preferably, the catalyst support is selected from the group consisting of carbon, $SiO_2$, and $Al_2O_3$. The more preferred catalyst support member is carbon. The most preferred catalyst support member is oxidatively stable carbon.

The metal catalyst of the invention can be selected from the group consisting of Group VII (Groups 8–10) of the Periodic Table of Elements, preferably selected from the group consisting of iridium, palladium, platinum, rhenium, rhodium and ruthenium and combinations thereof. More preferably the metal catalyst is ruthenium; most preferably supported on oxidatively stable carbon.

The process of the instant invention is preferably performed at a temperature from about 100° C. to about 200° C., more preferably at a temperature of about 140–160° C. The process is also preferably performed at a pressure of about 0.5 to about 10.0 MPa, more preferably at a pressure of about 4.0 to about 6.0 MPa. The process is also preferably carried out in a liquid phase.

The catalyst of the instant invention may optionally be promoted with at least one promoter, preferably where the promoter is a metal. Preferably, the promoter is selected from the group consisting of Group VII (Groups 8–10) and Group IB (Group 11) elements of the Periodic Table of Elements, more preferably gold, silver and copper.

DETAILED DESCRIPTION OF THE INVENTION

The invention is directed to a process for the preparation of 5-methylbutyrolactone, also known as 5-valerolactone or γ-valerolactone, from levulinic acid in the presence of a metal catalyst.

The catalyst of the invention can include one or more metals selected from Group VIII (Group 8-Group 10) elements from the Periodic Table of Elements, more preferably, the group consisting of iridium, palladium, platinum, rhenium, rhodium and ruthenium. The metal catalyst can optionally be supported on a catalyst support. The metal can be deposited on the support using any method known in the art. Preferably, the catalyst has about 1% to about 10% by weight of metal present on the support; more preferably about 5%.

Optionally, the catalyst can include one or more promoters. Preferably the promoter is also a metal, where the promoter is present in less than about 50 weight percent compared to the metal catalyst. More preferably the promoter is a Group VIII or a Group IB (Group 11) metal of the Periodic Table of Elements.

Each catalyst individually has both a hydrogenation and a ring-closing function; that is, the reaction proceeds in one step and produces little or none of the pentyl alcohols such as pentanediol.

The catalyst support can be any solid, inert substance including, but not limited to, metal oxides such as silica, alumina, and titania, and carbons. Preferred are carbons with a surface area greater than 200 $m^2/gm$. The catalyst support can be in the form of powder, granules, pellets, or the like.

"Oxidatively stable carbon" is hereby defined as carbon that exhibits substantial weight stability when heated in air. Such carbons are described further in International Publication WO 97/30932. More particularly, when the carbons are heated in air at 125° C. for 30 minutes, followed by heating at 200° C. for 30 minutes, followed by heating at 300° C. for 30 minutes, followed by heating at 350° C. for 45 minutes, followed by heating at 400° C. for 45 minutes, followed by heating at 450° C. for 45 minutes and finally followed by heating at 500° C. for 30 minutes, the carbons employed for the process of this invention lose less than 20% of their weight. This sequence of time and temperature conditions for evaluating the effect of heating carbon samples in air is defined herein as the "WVC Temperature Test". The WVC Temperature Test may be run using thermal gravimetric analysis (TGA). Carbons which when subjected to the WVC Temperature Test lose about 20% of their weight, or less, are considered to be advantageously oxidatively stable. Carbon from any of the following sources are useful for the process of this invention; wood, peat, coal, coconut shells, bones, lignite, petroleum-based residues and sugar. Commercially available carbons which may be used in this invention include those sold under the following trademarks: Barneby & Sutcliffe™, Darco™, Nuchar™, Columbia JXN™, Columbia LCK™, Calgon PCB™, Calgon BPL™, Westvaco™, Norit™ and Barnaby Cheny NB™.

The process is best performed at from about 50° C. to about 250° C., preferably 100° C. to about 200° C., and more preferably at about 140° C. to about 160° C. The process is performed at a pressure of about 5 to about 100 atmospheres (0.5 MPa to 10 MPa). Preferably the process is performed at a pressure of about 40 to about 60 atmospheres (4.0 to 6.0 MPa). The process is performed in an atmosphere of pure hydrogen gas, or a mixture of hydrogen with inert gases.

The process is preferably carried out in a liquid phase. The choice of solvent is not critical provided the solvent is not detrimental to catalyst, reactant and product. A preferred solvent is dioxane or 5-valerolactone. Preferred reactor designs are trickle bed and slurry.

The following Examples further illustrate the invention.

Materials and Methods

The following abbreviations and definitions are used herein:

| | |
|---|---|
| LA | Levulinic acid |
| 5-MGBL | 5-methyl-gamma-butyrolactone |

Catalyst supports used are listed below. The oxidatively stable carbon catalyst supports were tested for weight stability via thermogravimetric analysis according to the WVC Temperature Test.

| Support | Weight loss | Source |
|---|---|---|
| Sibunit carbon | 1.6% | Boreskov Inst. of Catalysis, Novosibirsk, Russia |
| Silica grade 55 | n.a. | W. R. Grace & Co., Columbia, MD |
| Calsicat carbon | 14.9% | Englehard Corp., E. Windsor, CT |
| Calgon PCB carbon | 49% | Nalco Chemical Co., Naperville, IL |
| $Al_2O_3$ | n.a. | Harshaw Chemical Co., Cleveland, OH |

EXAMPLES

The catalysts were prepared by impregnating the catalyst support by incipient wetness with a metal salt. The precursors used were $NiCl_2.6H_2O$ (Alfa Aesar, Ward Hill, Mass.), $Re_2O_7$ (Alfa), $PdCl_2$ (Alfa), $RuCl_3.xH_2O$ (Aldrich, Milwaukee, Wis.), $H_2PtCl_6$ (Johnson Matthey, Ward Hill, Mass.), 5% Rh using $RhCl_3.xH_2O$ (Alfa), $Re_2O_7$ (Alfa) and $IrCl_3.3H_2O$ (Johnson Matthey). The samples were dried and reduced at 400° C. in $H_2$ for 2 hours. The reaction was performed by placing the feedstock, 1 mL of a 50% solution of levulinic acid in dioxane with the listed amount of catalyst in a 2 ml pressure vessel. The vessel was charged with $H_2$ to 800 psi (5.5 MPa) for Examples 1–22 and 700 psi (4.8 MPa) for Examples 23–32, and heated to 215° C. for 2 hours. The sample was then cooled and vented and the product analyzed by GC-MS using methoxyethylether as an internal standard. Results are shown in Table 1 below. The column termed "LA Con" refers to LA Conversion, which is measured by subtracting the remaining amount of levulinic acid from the initial amount of levulinic acid (LA initially-LA remaining).

TABLE 1

| Ex. | $H_2$ (psi) | Catalyst | 5-MGBL Sel (%) | LA Con (%) | Feedstock (mg) | Catalyst (mg) |
|---|---|---|---|---|---|---|
| 1 | 700 | 5% Ir / $Al_2O_3$ | 70.3 | 36.3 | 974.5 | 103.2 |
| 2 | 700 | 5% Ir / Calgon C | 96.7 | 31.4 | 979.3 | 103.8 |
| 3 | 700 | 5% Ir / Calsicat C | 98.1 | 40.4 | 972.8 | 98 |
| 4 | 800 | 5% Ir / Calsicat C | 98.5 | 98.7 | 986.4 | 100.9 |
| 5 | 800 | 5% Ir / Calsicat C | 95.4 | 99.4 | 990.1 | 101 |
| 6 | 700 | 5% Ir / Sibunit C | 95.1 | 40.8 | 984.8 | 106.1 |
| 7 | 800 | 5% Ir / Sibunit C | 97.0 | 67.3 | 998.2 | 99.8 |
| 8 | 800 | 5% Ir / Sibunit C | 96.9 | 63.5 | 989.9 | 100.7 |
| 9 | 700 | 5% Ir / $SiO_2$ | 85.7 | 19.9 | 986.3 | 101.7 |
| 10 | 800 | 5% Pd / Calgon C | 89.0 | 15.7 | 967.5 | 99.1 |
| 11 | 800 | 5% Pd / Calsicat C | 92.4 | 32.1 | 982 | 100.4 |
| 12 | 800 | 5% Pd / Calsicat C | 96.8 | 69.4 | 976.6 | 98.6 |
| 13 | 800 | 5% Pd / Calsicat C | 91.5 | 66.8 | 991.8 | 99.7 |
| 14 | 800 | 5% Pd / Sibunit C | 82.2 | 16.3 | 981.3 | 102.3 |
| 15 | 800 | 5% Pd / $SiO_2$ | 67.0 | 17.7 | 1028.5 | 99 |
| 16 | 800 | 5% Pt / Calgon C | 72.1 | 25.3 | 1017.8 | 105.8 |
| 17 | 700 | 5% Pt / Calsicat C | 82.5 | 15.6 | 940.7 | 99.7 |
| 18 | 800 | 5% Pt / Sibunit C | 81.8 | 18.4 | 958.1 | 97.7 |
| 19 | 800 | 5% Pt / $SiO_2$ | 71.9 | 19.0 | 981.9 | 97.2 |
| 20 | 700 | 5% Re / Calgon C | 83.2 | 7.8 | 970 | 97.6 |
| 21 | 700 | 5% Re / Calsicat C | 82.3 | 8.9 | 961 | 97.9 |
| 22 | 700 | 5% Re / Sibunit C | 76.4 | 11.1 | 957 | 102.2 |
| 23 | 800 | 5% Rh / $Al_2O_3$ | 81.0 | 52.8 | 962.3 | 103.3 |
| 24 | 800 | 5% Rh / Calgon C | 96.1 | 62.1 | 989.9 | 105.2 |
| 25 | 700 | 5% Rh / Calsicat C | 97.6 | 30.7 | 934.8 | 100.4 |
| 26 | 800 | 5% Rh / Calsicat C | 96.0 | 99.9 | 990.6 | 100.9 |
| 27 | 800 | 5% Rh / Calsicat C | 96.1 | 100.0 | 986.1 | 98.3 |
| 28 | 800 | 5% Rh / Sibunit C | 82.1 | 54.8 | 982 | 102.7 |

TABLE 1-continued

| Ex. | H$_2$ (psi) | Catalyst | 5-MGBL Sel (%) | LA Con (%) | Feedstock (mg) | Catalyst (mg) |
|---|---|---|---|---|---|---|
| 29 | 800 | 5% Rh / Sibunit C | 97.3 | 97.6 | 993 | 102.2 |
| 30 | 800 | 5% Rh / Sibunit C | 97.5 | 96.4 | 990.1 | 100.8 |
| 31 | 800 | 5% Rh / SiO$_2$ | 83.9 | 43.3 | 993.2 | 97.4 |
| 32 | 800 | 5% Ru / Al$_2$O$_3$ | 64.7 | 42.3 | 999.9 | 96.8 |
| 33 | 800 | 5% Ru / Calgon C | 88.5 | 57.5 | 1010 | 103.2 |
| 34 | 800 | 5% Ru / Calgon C | 73.2 | 32.6 | 974.6 | 10.5 |
| 35 | 800 | 5% Ru / Calgon C | 67.6 | 59.9 | 975.1 | 10.7 |
| 36 | 800 | 5% Ru / Calsicat C | 92.2 | 81.0 | 987.6 | 97.8 |
| 37 | 800 | 5% Ru / Calsicat C | 73.5 | 50.0 | 1002 | 10 |
| 38 | 800 | 5% Ru / Calsicat C | 76.0 | 65.1 | 980.7 | 10.2 |
| 39 | 800 | 5% Ru / Calsicat C | 97.0 | 100.0 | 985.2 | 100.9 |
| 40 | 800 | 5% Ru / Calsicat C | 94.2 | 100.0 | 996.5 | 97.8 |
| 41 | 800 | 5% Ru / Sibunit C | 97.4 | 52.0 | 990.1 | 105.2 |
| 42 | 800 | 5% Ru / Sibunit C | 81.5 | 31.5 | 975.7 | 10.2 |
| 43 | 800 | 5% Ru / Sibunit C | 80.9 | 47.9 | 974.7 | 10.8 |
| 44 | 800 | 5% Ru / Sibunit C | 97.7 | 97.3 | 980.4 | 100 |
| 45 | 800 | 5% Ru / Sibunit C | 98.5 | 98.3 | 988.6 | 100.1 |
| 46 | 800 | 5% Ru / SiO$_2$ | 81.6 | 37.1 | 1010.9 | 99.3 |

What is claimed is:

1. A process for preparing 5-methylbutyrolactone comprising heating levulinic acid in the presence of hydrogen and a catalytic amount of a metal catalyst, said metal catalyst having both a hydrogenation and a ring-closing function, wherein the metal catalyst is selected from the group consisting of Group VIII of the Periodic Table of Elements.

2. The process as recited in claim 1 wherein the metal catalyst is supported on a catalyst support.

3. The process as recited in claim 2, wherein the catalyst support is selected from the group consisting of carbon, SiO$_2$, and Al$_2$O$_3$.

4. The process as recited in claim 3, wherein the carbon is oxidatively stable.

5. The process as recited in claim 1, wherein the metal catalyst is selected from the group consisting of platinum, rhenium, ruthenium, rhodium, iridium, palladium, and combinations thereof.

6. The process as recited in claim 5, wherein the metal catalyst is ruthenium.

7. The process as recited in claim 6, wherein the carbon is oxidatively stable.

8. The process as recited in claim 1, wherein said process is performed at a temperature from about 100° C. to about 200° C.

9. The process as recited in claim 1, wherein said process is performed at a temperature of about 140° C. to about 160° C.

10. The process as recited in claim 1, wherein said process is performed at a pressure of about 0.5 MPa to about 10.0 MPa.

11. The process as recited in claim 1, wherein said process is performed at a pressure of about 4.0 MPa to about 6.0 MPa.

12. The process as recited in claim 1, wherein the process is carried out in a liquid phase.

13. The process as recited in claim 1, wherein the metal catalyst is optionally promoted with at least one promoter.

14. The process as recited in claim 13, wherein the promoter is a metal.

15. The process as recited in claim 14, wherein the promoter is selected from the group consisting of Group VIII and Group IB elements of the Periodic Table of Elements.

* * * * *